(12) United States Patent
Park et al.

(10) Patent No.: US 11,675,421 B1
(45) Date of Patent: Jun. 13, 2023

(54) TIME-MULTIPLEXING RESONANT DRIVE SCHEME TO GENERATE DUAL POLARITY SUPPLIES

(71) Applicant: MICROSOFT TECHNOLOGY LICENSING, LLC, Redmond, WA (US)

(72) Inventors: Chang Joon Park, Sunnyvale, CA (US); Martin Francis Galinski, III, Santa Clara, CA (US)

(73) Assignee: MICROSOFT TECHNOLOGY LICENSING, LLC, Redmond, WA (US)

(*) Notice: Subject to any disclaimer, the term of this patent is extended or adjusted under 35 U.S.C. 154(b) by 0 days.

(21) Appl. No.: 17/561,282

(22) Filed: Dec. 23, 2021

(51) Int. Cl.
*G06F 3/01* (2006.01)
*G06V 40/16* (2022.01)
(Continued)

(52) U.S. Cl.
CPC ............ *G06F 3/011* (2013.01); *A61B 5/16* (2013.01); *G01D 5/24* (2013.01); *G06F 1/163* (2013.01);
(Continued)

(58) Field of Classification Search
CPC .......... G02B 27/017; G02B 2027/0178; G02B 2027/087; G02B 2027/014; H04B 1/385; H04B 1/38; H02J 7/0063; H02J 7/0019; G06F 3/013; G06F 3/011; G06F 3/012; G06F 3/015; G06F 3/03; G06F 3/0416; G06F 3/04815; G06F 1/163; G06V 40/174; G06V 40/171; G06V 40/168; G06V 40/169; G06V 40/175; G06V 40/176;
(Continued)

(56) References Cited

U.S. PATENT DOCUMENTS

| 2009/0219039 A1 | 9/2009 | Fasshauer | |
| 2012/0229248 A1* | 9/2012 | Parshionikar | .......... G08B 21/06 340/3.1 |

(Continued)

FOREIGN PATENT DOCUMENTS

WO 2021090697 A1 5/2021

OTHER PUBLICATIONS

"International Search Report and Written Opinion Issued in PCT Application No. PCT/US22/047963", dated Feb. 17, 2023, 9 Pages.

*Primary Examiner* — Dismery Mercedes
(74) *Attorney, Agent, or Firm* — Brett A. Hertzberg; Newport IP, LLC

(57) ABSTRACT

A time-multiplexing resonant drive scheme is described that reuses an inductor circuit for multiple functional purposes in a Mixed Reality (MR) device. A driver circuit and a multiplexer circuit are dynamically configured by a controller circuit for three operating modes. In the first mode, energy is coupled from a battery to the inductor circuit in a forward direction to charge the inductor circuit and generate a positive power supply voltage. In the second mode, energy is coupled from to the inductor circuit in a reverse direction to charge the inductor circuit and generate a negative power supply voltage. In the third mode, the inductor is operated with an antenna as part of a resonance drive circuit, where facial movements of the user can be detected based on the response. Reduced component count and reduced cost requirements are achieved by the described scheme.

20 Claims, 8 Drawing Sheets

(51) Int. Cl.
  *G01D 5/24* (2006.01)
  *G06F 1/16* (2006.01)
  *H02J 7/00* (2006.01)
  *A61B 5/16* (2006.01)

(52) U.S. Cl.
  CPC .............. *G06F 3/012* (2013.01); *G06F 3/015* (2013.01); *G06V 40/16* (2022.01); *G06V 40/174* (2022.01); *G06V 40/176* (2022.01); *H02J 7/0063* (2013.01)

(58) Field of Classification Search
  CPC ........ G06V 40/20; G06V 40/16; G06V 40/23; G06V 40/1306; A61B 5/165; A61B 5/163; A61B 5/388; A61B 5/369; A61B 5/6802; A61B 5/7264; G01D 5/24; G08B 21/06; A61N 1/0476; A61N 1/36031
  See application file for complete search history.

(56) References Cited

U.S. PATENT DOCUMENTS

| | | | |
|---|---|---|---|
| 2012/0254244 A1* | 10/2012 | Vetek | G06V 40/176 707/E17.014 |
| 2015/0295450 A1* | 10/2015 | Bae | H02J 50/12 320/108 |
| 2016/0254679 A1* | 9/2016 | Liu | H02J 50/12 307/104 |
| 2017/0307891 A1* | 10/2017 | Bucknor | G02B 27/0093 |
| 2019/0229771 A1* | 7/2019 | Lee | H02J 50/90 |
| 2019/0245387 A1* | 8/2019 | Park | H02J 50/12 |
| 2021/0019034 A1* | 1/2021 | Kim | G06F 3/0446 |
| 2021/0083524 A1* | 3/2021 | Mynar | H02J 50/60 |
| 2021/0089265 A1* | 3/2021 | van Erven | G06F 3/167 |
| 2021/0138232 A1* | 5/2021 | Paz | A61N 1/36031 |
| 2021/0248358 A1* | 8/2021 | Lee | G06K 9/6219 |
| 2022/0137702 A1* | 5/2022 | Min | G06F 3/012 345/156 |

* cited by examiner

TIME-MULTIPLEXING RESONANT DRIVE SCHEME TO GENERATE DUAL POLARITY SUPPLIES

BACKGROUND

Mixed Reality (MR), like Augmented Reality (AR) and Virtual Reality (VR), is an industry with a rapidly expanding footprint. An MR device may be implemented with a headset that includes video and audio components to provide the immersive MR experience. Sensors, such as gyroscopic sensors, may be located on or within the headset to sense physical movement of the user. Additional sensors may be located about the headset to track eye gaze of the user, sense audible commands from the user, and to sense other aspects of the user.

Various face tracking schemes that may be employed to sense small movements of the user's skin, which can be processed to identify facial expression and other indicia that may be used to enhance the immersive MR experience. In one example scheme, a headset may be equipped with circuits that include a number of sense antennas that are positioned about various locations of the headset. The antennas signals may feed into an LC resonance circuit, which is driven to a resonance by an LC driver. The output of the LC resonance circuit may feed into a sense amplifier to provide suitable signals for an Analog-to-Digital Converter (ADC), which can convert the sensed signals into the digital domain for further processing. Capacitance of the LC resonance circuit varies depending on the distance between the sense antennas on the headset and the facial skin of the user. The distance between the skin and the antennas varies may also vary with the facial expression of the user due to movement of the skin from facial muscles. Thus, the total capacitance of the LC resonance circuit, and thus the characteristic transient response and Q of the LC resonance circuit, will vary based on the user's facial movements and the resulting varied distance between the antennas and the user's skin.

The present disclosure contemplates that a conventional implementation of an LC resonant drive circuit may require relatively high power-supply levels when compared to a typical battery in a portable device. This is in part due to the overall design of a conventional system, where the amplitude of the sensed signal from the LC resonance circuit should be as large as possible to maximize the overall dynamic range and resolution that may be achieved in an analog-to-digital conversion process.

The presently disclosed techniques propose solutions for MR wearable devices to achieve sufficient resolution without requiring the additional of expensive boost circuits to generate the dual supply voltages needed to operate the circuits required to detect facial movements of the user. Circuit complexity is reduced, and the overall cost of the solution is reduced. The disclosure made herein is presented with respect to these and other technical challenges.

SUMMARY

The techniques disclosed herein are directed to devices, circuits, systems and methods for facial movement detection with reduced component count, reduced size, and reduced cost by employing a novel time-multiplexing scheme. An example battery operated system includes a driver circuit, an inductor circuit, a multiplexer circuit, and one or more antennas. A time-multiplexing resonant drive scheme is described that reuses the inductor circuit for multiple functional purposes. The driver circuit and the multiplexer circuit are dynamically configured by a controller circuit for three operating modes. In the first mode, energy is coupled from a battery to the inductor circuit in a forward direction to charge the inductor circuit and generate a positive power supply voltage. In the second mode, energy is coupled from to the inductor circuit in a reverse direction to charge the inductor circuit and generate a negative power supply voltage. In the third mode, the inductor is operated with an antenna as part of a resonance drive circuit, where facial movements of the user can be detected based on the response. Reduced component count and reduced cost requirements are achieved by the described scheme.

The described embodiments may be implemented as devices, circuits, and systems, which may include software. This Summary is provided to introduce a selection of concepts in a simplified form that are further described below. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The Detailed Description is described with reference to the accompanying figures. References made to individual items of a plurality of items can use a reference number with a letter of a sequence of letters to refer to each individual item. Generic references to the items may use the specific reference number without the sequence of letters.

DETAILED DESCRIPTION

Figure 1:
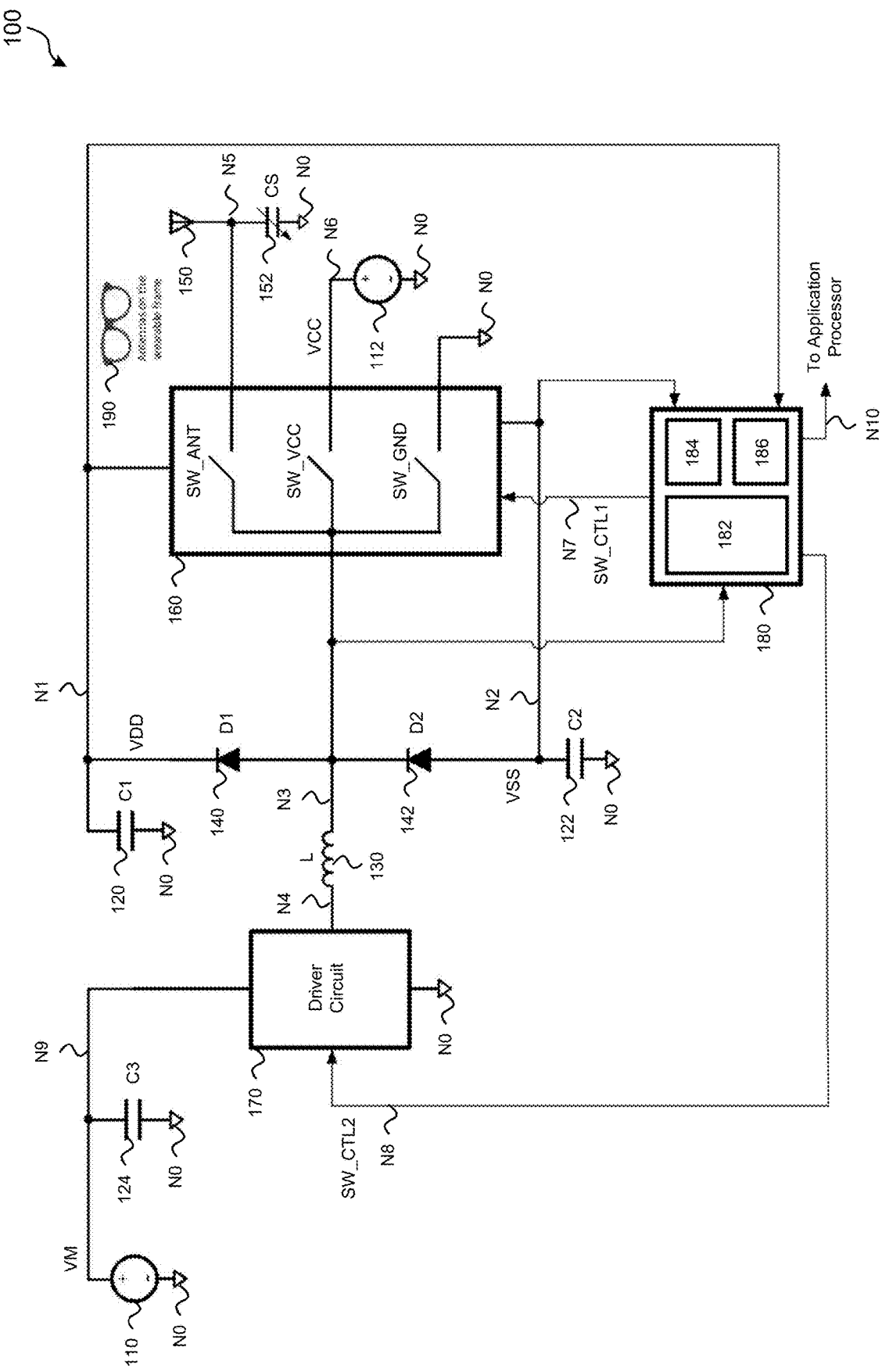
FIG. 1 shows an illustrative schematic of a first system that employs a time-multiplexing resonant drive scheme to generate dual polarity supplies in an LC resonance circuit, which can be used in RF facial detection applications.

In the following detailed description, reference is made to the accompanied drawings, which form a part hereof, and which is shown by way of illustration, specific example configurations of which the concepts can be practiced. These configurations are described in sufficient detail to enable those skilled in the art to practice the techniques disclosed herein, and it is to be understood that other configurations can be utilized, and other changes may be made, without departing from the spirit or scope of the presented concepts. The following detailed description is, therefore, not to be taken in a limiting sense, and the scope of the presented concepts is defined only by the appended claims.

Throughout the specification and claims, the following terms take the meanings explicitly associated herein, unless the context clearly dictates otherwise. The meaning of "a," "an," and "the" includes plural reference, the meaning of "in" includes "in" and "on." The term "connected" means a direct electrical connection between the items connected, without any intermediate devices. The term "coupled" means a direct electrical connection between the items connected, or an indirect connection through one or more passive or active intermediary devices and/or components. The terms "circuit" and "component" means either a single component or a multiplicity of components, either active and/or passive, that are coupled to provide a desired function. The term "signal" means at least a power, current, voltage, or data signal. Based upon context, the term "coupled" may refer to a wave or field coupling effect, which may relate to a corresponding magnetic field, electrical field, or a combined electromagnetic field.

Mixed Reality (MR), like Augmented Reality (AR) and Virtual Reality (VR), is an industry that has rapidly expanded its footprint. Compact form factor is an important design issue in such wearable devices, which require portability. To achieve better portability, a scheme can be employed so that some of the required circuit components can be reused and shared in function between multiple circuits, which results in improved area efficiency and reduced overall cost.

An LC resonant drive circuit is an example circuit that is a good candidate for reduced componentry by sharing of components for multiple functions. An LC resonant driving scheme is one of the best candidates for a low power target since the signal will be boosted at the target frequency due to the nature of LC resonant principle. It helps the device reliability and safety aspects. In addition, the inductor from the LC resonant drive circuit can be reused or shared with other circuits to generate the higher power supply voltages since the inductor is an energy storage device. The present disclosure contemplates that the total number of components used in the whole system should be reduced for a compact form factor since the inductor is bulky component in the circuit.

The LC resonant drive circuit doesn't need to run all the time, only during certain modes of operation. For example, the LC resonant drive circuit can be activated in one time period when the sensors are driven to get the sense signals in the RF facial detection scheme, and then in another time period the inductor can be reused for the dual polarity supply generation, thus employing a time-multiplexing scheme for the inductor. A time-multiplexing scheme helps to share the same circuit blocks as half-bridge resonator (e.g., FETs and inductor) for the sensor and power solution.

A conventional LC resonant drive circuit for a sensor solution like an RF face tracking scheme requires higher power supply voltages since the amplitude of the sensed signal that will be processed by Analog-to-Digital Converter (ADC) that integrated in Microprocessor or Application Specific Integrated Circuit (ASIC) should be large as much as possible to achieve higher resolution. Therefore, the proposed time-multiplexing resonant drive scheme to generate dual polarity supplies might be one of the best approaches to realize the sensor.

FIG. 1 shows an illustrative schematic of a first system 100 that employs a time-multiplexing resonant drive scheme to generate dual polarity supplies in an LC resonance circuit, which can be used in RF facial detection applications. As illustrated, system 100 includes a battery 110, a DC source 112, a first capacitor circuit 120, a second capacitor circuit 122, a third capacitor circuit 124, an inductor circuit 130, a first diode circuit 140, a second diode circuit 142, an antenna 150, a sense capacitor 152, a multiplexer (MUX) 160, a driver circuit 170, and a controller circuit 180. The antenna 150 may be positioned about various locations of a wearable MR headset, such as a wearable frame 190.

Node N0 is designated as a circuit ground (e.g., GND). The battery 110 is coupled between node N9 and node N0, and provides a battery voltage corresponding to VM at node N9. The DC source 112 is coupled between node N6 and node N0, and provides a voltage VCC at node N6. The first capacitor circuit 120 is coupled between node N1 and node N0, and is designated as C1. The second capacitor circuit 122 is coupled between node N2 and node N0, and is designated as C2. The third capacitor circuit 124 is coupled between node N9 and node N0, and is designated as C3. Inductor circuit 130 is coupled between node N3 and node N4, and is designated as L. The first diode circuit 140 is couple between node N3 and node N1, and is designated as D1. The second diode circuit 142 is couple between node N2 and node N3, and is designated as D2. The antenna 150 is coupled to node N5, and has a characteristic capacitance that corresponds to the sense capacitor 152. Sense capacitor 152 is coupled between node N5 and node N0, and is designated as CS. MUX 160 includes an input port (e.g., IN) at node N3, a first output port (e.g., OUT1) at node N5, a second output port (e.g., OUT2) at node N6, a third output port (e.g., OUT3) at node N0, a first power port (e.g., VDD) at node N1, a second power port (e.g., VSS) at node N2, and a control port (e.g., CTL) at node N7. The driver circuit 170 includes an output port (e.g., OUT) at node N4, a first power port (e.g., VM) at node N9, a second power port (e.g., GND) at node N0, and a control port (e.g., CTL) at node N8. The controller circuit 180 includes a first input port (e.g., IN1) at node N1, a second input port (e.g., IN2) at node N2, a third input port (e.g., IN3) at node N3, a first output port (e.g., OUT1) at node N7, a second output port (e.g., OUT2) at node N8, and a third output port (e.g., OUT3) at node N10.

Operationally, node N1 corresponds to the positive power supply voltage VDD, node N2 corresponds to the negative power supply voltage VSS, node N7 corresponds to a first switch control signal SW_CTL1, node N8 corresponds to a second switch control signal SW_CTL2, and node N10 corresponds to an output of the MCU that can be communicated to an application processor (e.g., for Facial Tracking, etc.). The control port (CTL) of MUX 160 will selectively couple the input port (IN, node N3) to one of the output ports (OUT1, N7; OUT2, N6; OUT3, N0), responsive to the input received from the control port (CTL) at node N7, which corresponds to the first switch control signal SW_CTL1. The driver circuit 170 is configured by the second switch control signal SW_CTL2 to selectively couple power to the inductor circuit 13, either from the battery voltage VM at node N9 or to the circuit ground at node N0. The operation of the MUX 160 together with the driver circuit 170, is effective to time-multiplex the charging and discharging of the inductor circuit 130 at node N3 to either the antenna 150 at node N7, the DC source 112 at node N6, or the circuit ground at node N0. In some examples, the voltage VCC at node N6 from the DC source 112 corresponds to the battery voltage VM at node N9.

MUX 160 is illustrated as including three switch circuits. A first switch circuit includes an input at node N3, an output at node N5, and is responsive to a first control signal SW_ANT. A second switch circuit includes an input at node N3, an output at node N6, and is responsive to a second control signal SW_VCC. A third switch circuit includes an input at node N3, an output at node N0, and is responsive to a third control signal SW_GND. The first switch control signal SW_CTL1 in FIG. 1 can either include multiple individual switch control signals, or be decoded by logic into the individual switch control signals SW_ANT, SW_VCC, and SW_GND.

The sense capacitor 152 is illustrated as a capacitor with a variable capacitance value (CS) that is coupled between node N5 and node N0 (e.g., GND). Although shown as a physical capacitor component, sense capacitor 152 corresponds to the characteristic capacitance of the antenna 150. Since the antenna is physically located on a wearable frame 190, the actual capacitance value (CS) of the antenna will vary based on proximity to the skin of the user. The inductor circuit 130 is effectively coupled in series between the output of the driver circuit 170 and the antenna 150. From node N4 looking through the inductor circuit 130 towards the sense capacitor 152, an LC filter circuit may be identified.

The controller circuit 180 may, in some examples, be implemented as a microcontroller unit (MCU). The MCU can be configured via software or firmware instructions to control the operation of the circuit 100 according to a time-division multiplexing scheme that includes three basic modes: charging in a positive direction (a first mode), charging in a negative direction (a second mode), and operating the antenna as a sensor in facial movement detection (a third mode). In some examples, the MCU may include a controller core 182, an analog to digital converter (ADC) 184 and one or more pulse or clock generators 186. The time-multiplexing operation of circuit 100 will become more apparent from further discussions found below.

In the first mode, the controller circuit 180 activates a first configuration of the driver circuit 170 via the second control signal SW_CTL2, which couples node N4 to node N9 such that node N4 effectively corresponds to the battery voltage VM. Also in this first mode, the controller circuit 180 pulse modulates a first switch configuration for MUX 160 via the first control signal SW_CTL1 (via SW_GND), which selectively couples node N3 to node N0 via the third switch circuit in MUX 160. On the high cycle of the pulse, node N3 is coupled to the circuit ground at node N0 such that the inductor circuit 130 is charged in a positive direction from node N4 to node N3. On the low cycle of the pulse, node N3 is decoupled from node N0 (e.g., a high impedance or open circuit condition), and the stored current from the inductor circuit 130 flows through the first diode circuit 140 to deliver charge to the first capacitor circuit 120 (C1). Over time, the repeated pulses will result in an accumulation of charge on the first capacitor circuit 120 (C1) sufficient to generate the positive power supply voltage VDD at node N1.

During the second mode, the controller circuit 180 activates a second driver configuration of the driver circuit 170 via the second control signal SW_CTL2, which couples node N4 to node N0 such that node N4 effectively corresponds to the circuit ground (e.g., 0V). Also, in this second mode, the controller circuit 180 pulse modulates a second switch configuration for MUX 160 via the first control signal SW_CTL1 (via SW_VCC), which selectively couples node N3 to node N6 via the second switch circuit in MUX 160. On the high cycle of the pulse, node N3 is coupled to the DC source 112 at node N6 such that the inductor circuit 130 is charged in a negative direction from node N3 to node N4. On the low cycle of the pulse, node N3 is decoupled from node N6 (e.g., a high impedance or open circuit condition), and the stored current from the inductor circuit 130 flows through the second diode circuit 140 to deliver charge to the second capacitor circuit 122 (C2). Over time, the repeated pulses will result in an accumulation of charge on the second capacitor circuit 122 (C2) sufficient to generate the negative power supply voltage VSS at node N2.

In some examples, the controller circuit 180 is configured to monitor the voltages at nodes N1 and N2 (e.g., via an ADC and/or other circuits to scale the voltage) to determine when the desired voltage is achieved at node N1. In other examples, additional circuitry (e.g., a comparator, voltage divider or gain scaler, etc.) may be used to determine when the desired voltage is achieved and notify the controller accordingly.

During the third mode, the controller circuit 180 selects a third switch configuration for MUX 160 via the first control signal SW_CTL1 (via SW_ANT), which couples node N3 to node N5 via switch the first switch circuit in MUX 160. Also in this third mode, the controller circuit 180 also selectively activates the driver circuit 170 via the second control signal SW_CTL2, which pulse modulates the coupling of node N4 between node N9 and node N0. In this third mode, the inductor circuit 130 is coupled to the antenna 150 and its characteristic sense capacitor 152 (CS) to form an LC resonant circuit. By pulse modulating the coupling of node N4 between node N9 and node N0, the LC resonant circuit is excited to generate an oscillating signal at node N3 which can be observed for face tracking. The dual supply voltages (VDD, VSS) previously generated in the first and second modes are used to operate the various circuits, while the LC resonant circuit is excited in this third mode. Based on the high Q resonance characteristics of the LC filter, the transient response will correspond to an AC signal at node N3.

The controller circuit 180 can be configured to capture the sensed signal from node N3 (e.g., via an Analog-to-Digital Converter, or ADC) which can then be provided as a digital signal at node N10 and to other systems for further processing (e.g., processing to determine facial expression, movement, etc.). The sensed signal may have a significantly high peak to peak voltage due to the high Q nature of the LC filter. Thus, additional circuitry (not shown in FIG. 1) may be required to scale down the signal size before being evaluated by the controller circuit 180.

The proposed technologies of FIG. 1 and others found herein illustrate a dual purpose inductor configuration that is used both for generation of the DC voltages supplies as well as for a DC-AC converter that is used for RF facial movement detection, which is suitable for use in portable systems that operate on battery power. The proposed systems also include an LC filter (or resonator) with a high quality factor (or Q), where the LC filter uses a series inductor circuit in conjunction with a sense capacitor that is formed by a sense antenna and facial skin from the user. The LC filter is configured to amplify the AC voltage of the AC power at a resonant frequency of the RF face tracking system. An important aspect of the proposed scheme is that the face tracking system benefits from reduced circuit complexity. In terms of the area and reduce complexity, there should be huge benefits as will be described herein.

The resonance frequency of the LC filter will change with variations in the sense capacitor from the antenna, which changes responsive to facial movement relative to the location of the antenna. For a given fixed input frequency, the gain and phase of the output signals from the LC filter will change with sensed capacitance variations. Very large output signals (e.g., in a range of about 20Vp-p to about 50Vp-p) can be achieved with a relatively small input signals (e.g., in a range of about 1Vp-p to about 5Vp-p) due to the peak gain and high Q at the resonant frequency of the LC filter.

Figure 2:
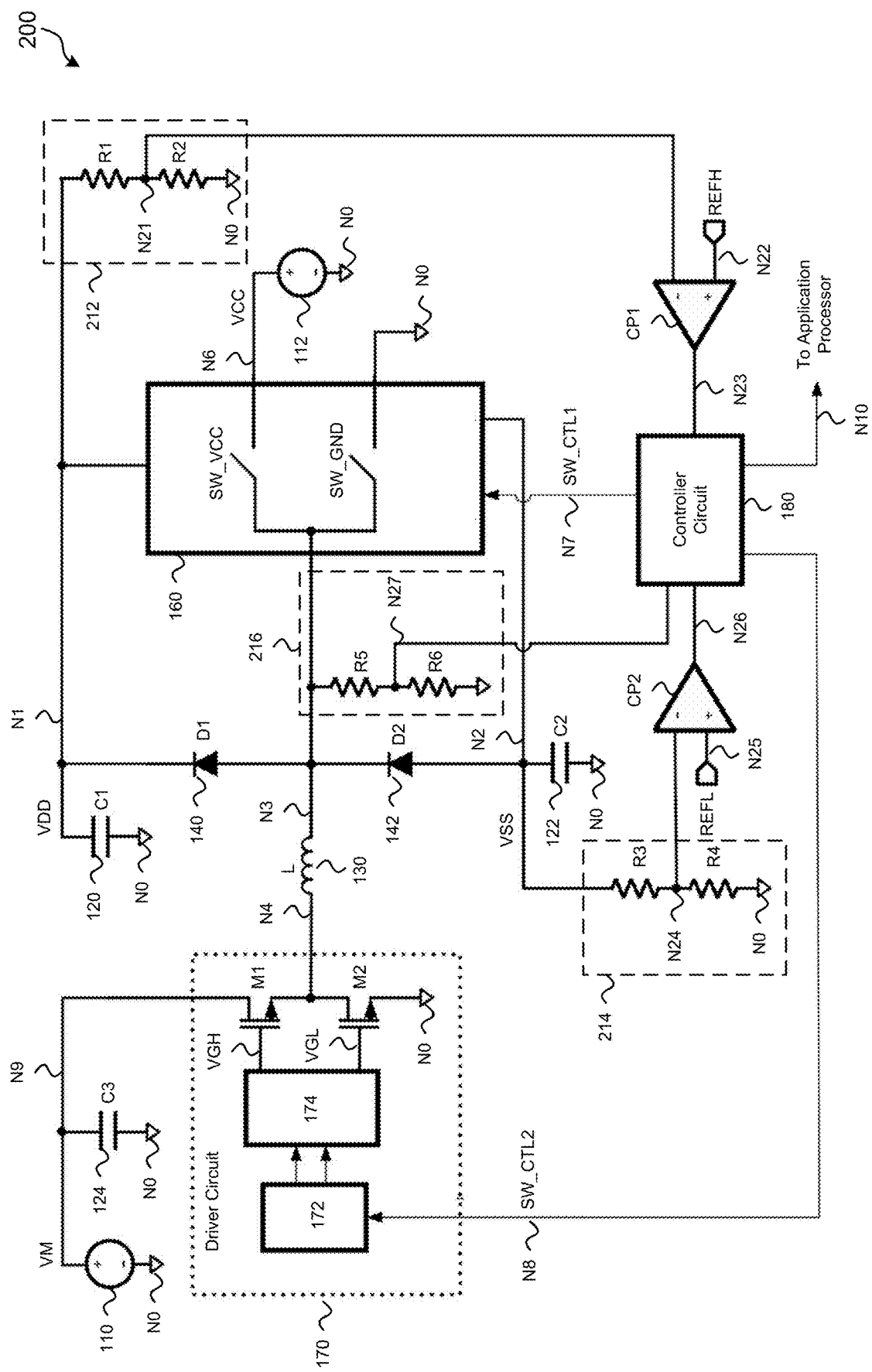
FIG. 2 shows an illustrative schematic of a second system that employs a time-multiplexing resonant drive scheme to generate dual polarity supplies in an LC resonance circuit, which can be used in RF facial detection applications.

FIG. 2 shows an illustrative schematic of a second system 200 that employs a time-multiplexing resonant drive scheme to generate dual polarity supplies in an LC resonance circuit, which can be used in RF facial detection applications. As illustrated, system 200 includes a battery 110, a DC source 112, a first capacitor circuit 120, a second capacitor circuit 122, a third capacitor circuit 124, an inductor circuit 130, a first diode circuit 140, a second diode circuit 142, a multiplexer (MUX) 160, a driver circuit 170, and a controller circuit 180. The system 200 of FIG. 2 does not show the wearable frame, antenna, sense capacitor and associated switches in the multiplexer, but such examples can be arranged similar to that shown in FIG. 1 and other figures found herein without departing from the spirit of the present disclosure.

Node N0 is designated as a circuit ground (e.g., GND). The battery 110 is coupled between node N9 and node N0, and provides a battery voltage corresponding to VM at node N9. The DC source 112 is coupled between node N6 and node N0, and provides a voltage VCC at node N6. The first capacitor circuit 120 is coupled between node N1 and node N0, and is designated as C1. The second capacitor circuit 122 is coupled between node N2 and node N0, and is designated as C2. The third capacitor circuit 124 is coupled between node N9 and node N0, and is designated as C3. Inductor circuit 130 is coupled between node N3 and node N4, and is designated as L. The first diode circuit 140 is couple between node N3 and node N1, and is designated as D1. The second diode circuit 142 is couple between node N2 and node N3, and is designated as D2. MUX 160 includes an input port (e.g., IN) at node N3, a first output port (e.g., OUT1) at node N5, a second output port (e.g., OUT2) at node N6, a first power port (e.g., VDD) at node N1, a second power port (e.g., VSS) at node N2, and a control port (e.g., CTL) at node N7. The driver circuit 170 includes an output port (e.g., OUT) at node N4, a first power port (e.g., VM) at node N9, a second power port (e.g., GND) at node N0, and a control port (e.g., CTL) at node N8. The controller circuit 180 includes a first input port (e.g., IN1) at node N23, a second input port (e.g., IN2) at node N26, a third input port (e.g., IN3) at node N27, a first output port (e.g., OUT1) at node N7, a second output port (e.g., OUT2) at node N8, and a third output port (e.g., OUT3) at node N10.

The operation of like labelled components is similar to that of FIG. 1 described previously above and will be omitted here for brevity. However, additional implementation examples are added in FIG. 2, which will now be described below.

The system of FIG. 2 further includes two comparators CP1 and CP2, and three voltage divider or scaler circuits (212, 214 and 216). A first voltage divider circuit 212 includes two resistors R1, R2 that are series coupled between node N1 and node N0, with the output of the first voltage divider circuit corresponding to node N21. The first comparator CP1 includes an inverting input (−) coupled to node N21, a non-inverting input (+) coupled to node N22, and an output coupled to node N23. A second voltage divider circuit 214 includes two resistors R3, R4 that are series coupled between node N2 and node N0, with the output of the second voltage divider circuit corresponding to node N24. The second comparator CP2 includes an inverting input (−) coupled to node N24, a non-inverting input (+) coupled to node N25, and an output coupled to node N26. A third voltage divider circuit 216 includes two resistors R5, R6 that are series coupled between node N3 and node N0, with the output of the second voltage divider circuit corresponding to node N27.

The voltage divider circuits described above are configured to scale the voltage from the corresponding one of the input nodes down to a suitable level for further processing. For example, the first voltage divider circuit formed by resistors R1 and R2 sense the voltage at node N1 and generate a scaled version of the sensed voltage at node N21. Similarly, the second voltage divider circuit formed by resistors R3 and R4 sense the voltage at node N2 and generate a scaled version of the sensed voltage at node N24; while the third voltage divider circuit formed by resistors R5 and R6 sense the voltage at node N3 and generate a scaled version of the sensed voltage at node N27.

Comparators CP1 and CP2 are configured to sense when the corresponding voltages at their inputs have achieved their target voltages. For example, the first comparator CP1 is configured to compare the sensed voltage (e.g., VSNSH) at node N21 to a first reference voltage REFH and generate a signal (e.g., VH) at node N23 to indicate (e.g., logic low indicates VDD reached a desired value) when the sensed voltage has reached REFH. Similarly, the second comparator CP2 is configured to compare the sensed voltage (e.g., VSNSL) at node N24 to a second reference voltage REFL and generate a signal (e.g., VL) at node N26 to indicate (e.g., logic high indicates that VSS reached a desired value) when the sense voltage has reached REFL. The controller circuit 180 uses these signals (e.g., VH and VL) from nodes N23 and N26 as inputs to control the timing and duty cycle of the charging of the inductor circuit 130. The polarities of either of these signals (e.g., VH and VL) could be reversed for any desired implementation by changing the inputs from the inverting to non-inverting inputs, without departing from the spirit of the present disclosure.

The output of the third voltage divider circuit 216 is shown as coupled to an input of the controller circuit 180 at node N27. This input corresponds to the scaled version of the sensed voltage from node N3. Operationally, the voltage at node N3 may represent the response of an LC resonance circuit, such as the LC resonance circuit shown in FIG. 1 by inductor 130 and sense capacitance 152, which is active when the multiplexer circuit 160 couples Node N3 to node N5 via switch SW_ANT. The response of the LC resonance circuit, as measured at node N27, can be converted into a digital value by ADC 184 in the controller circuit 180 (see FIG. 1).

A detailed implementation of the driver circuit 170 is also illustrated in FIG. 2, which includes a logic block 172, a gate driver block 174, FET M1 and FET M2. The logic block 172 includes an input port coupled to node N8, and a pair of outputs coupled to the gate driver block 174. Gate driver block 177 includes a first output (VGH) that is coupled to a gate of FET M1, and a second output (VGL) that is coupled a gate of FET M2. FET M1 further includes a drain coupled to node N9 and as source coupled to node N4. SFET M2 further includes a drain coupled to node N4 and as source coupled to node N0. Operationally, the signal at node N8 may represent a single control signal or multiple control signals (e.g., a multi-bit control signal), which controls the timing and duty cycle of the charging of the inductor via the driver circuit 170.

Figure 3:
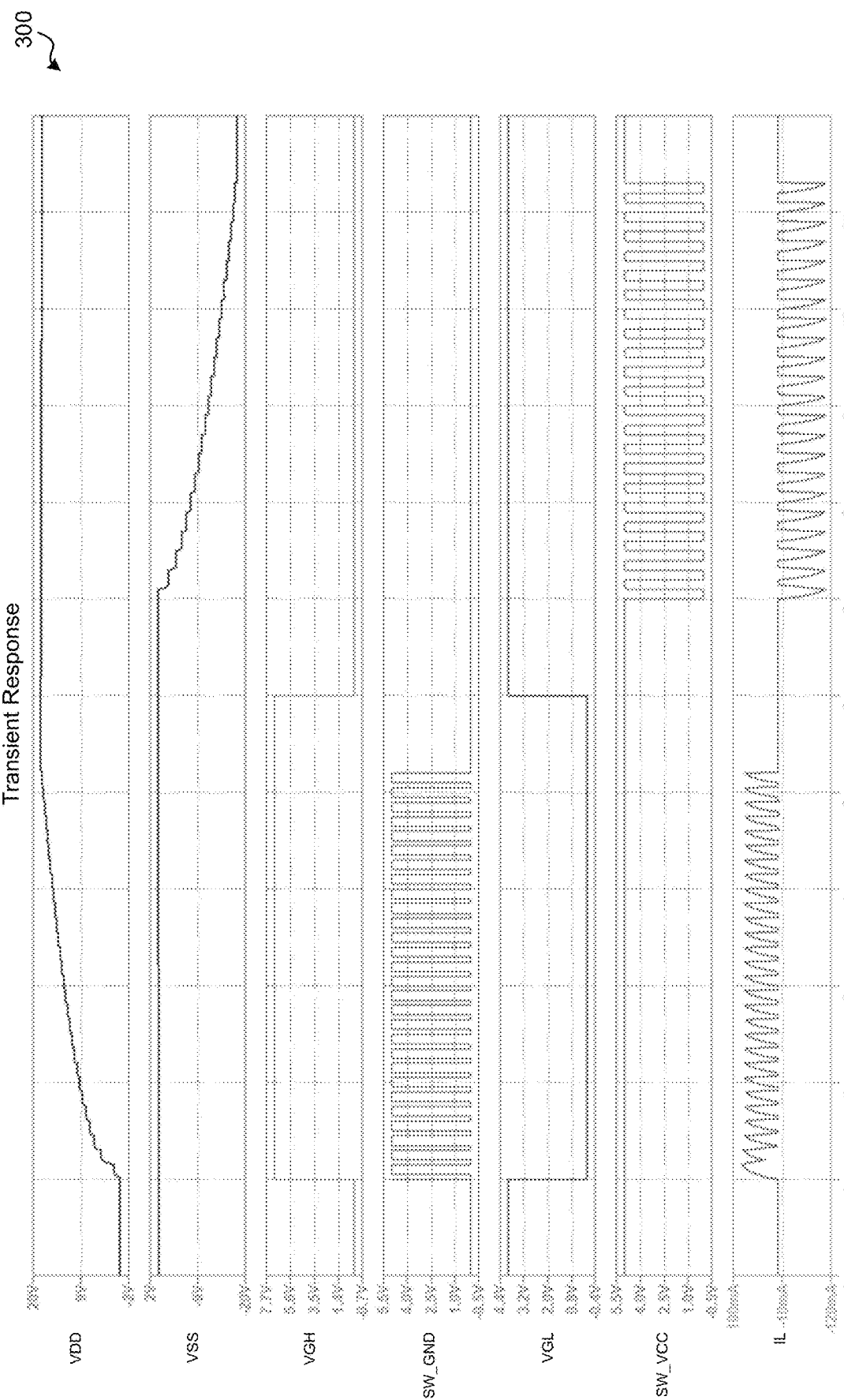
FIG. 3 shows a set of graphs illustrating a transient response for an example time-multiplexing resonant drive scheme.

FIG. 3 shows a set of graphs 300 illustrating a transient response for an example time-multiplexing resonant drive scheme such as for the example systems of FIGS. 1 and 2. FIG. 3 includes voltage waveforms for the dual supplies (VDD, VSS), high and low gate control signals (VGH, VGL) for the driver circuit 170, first and second switch control signals (SW_GND, SW_VCC) for the multiplexer circuit 160, and a current waveform for current (IL) flowing in the inductor circuit 130. These waveforms will be further described with reference to FIGS. 4A and 4B below.

Figure 4A:
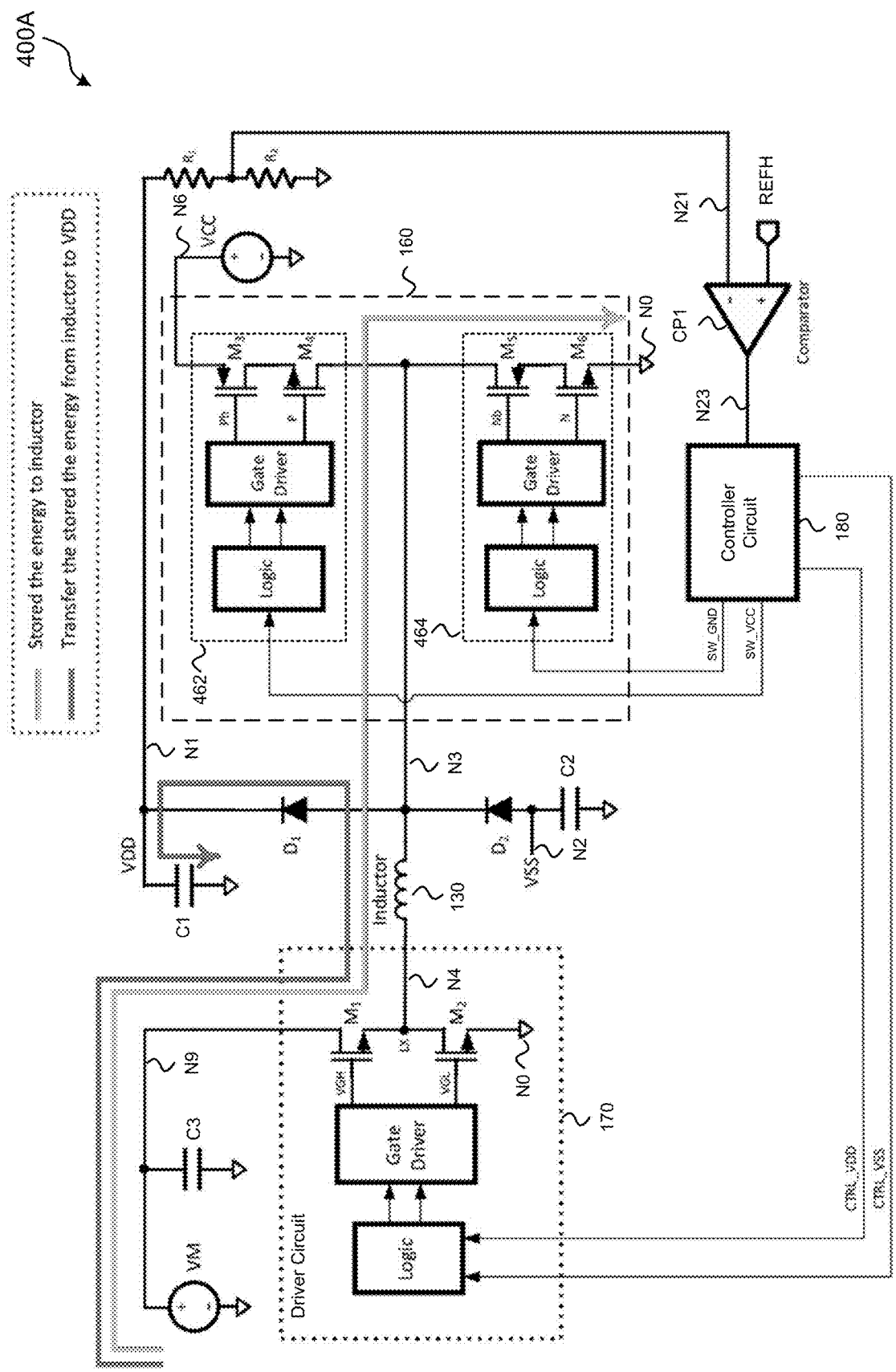
FIG. 4A shows an illustrative schematic that illustrates a first part of the operation of a third example time-multiplexing resonant drive scheme to generate dual polarity supplies in an LC resonance circuit.
Figure 4B:
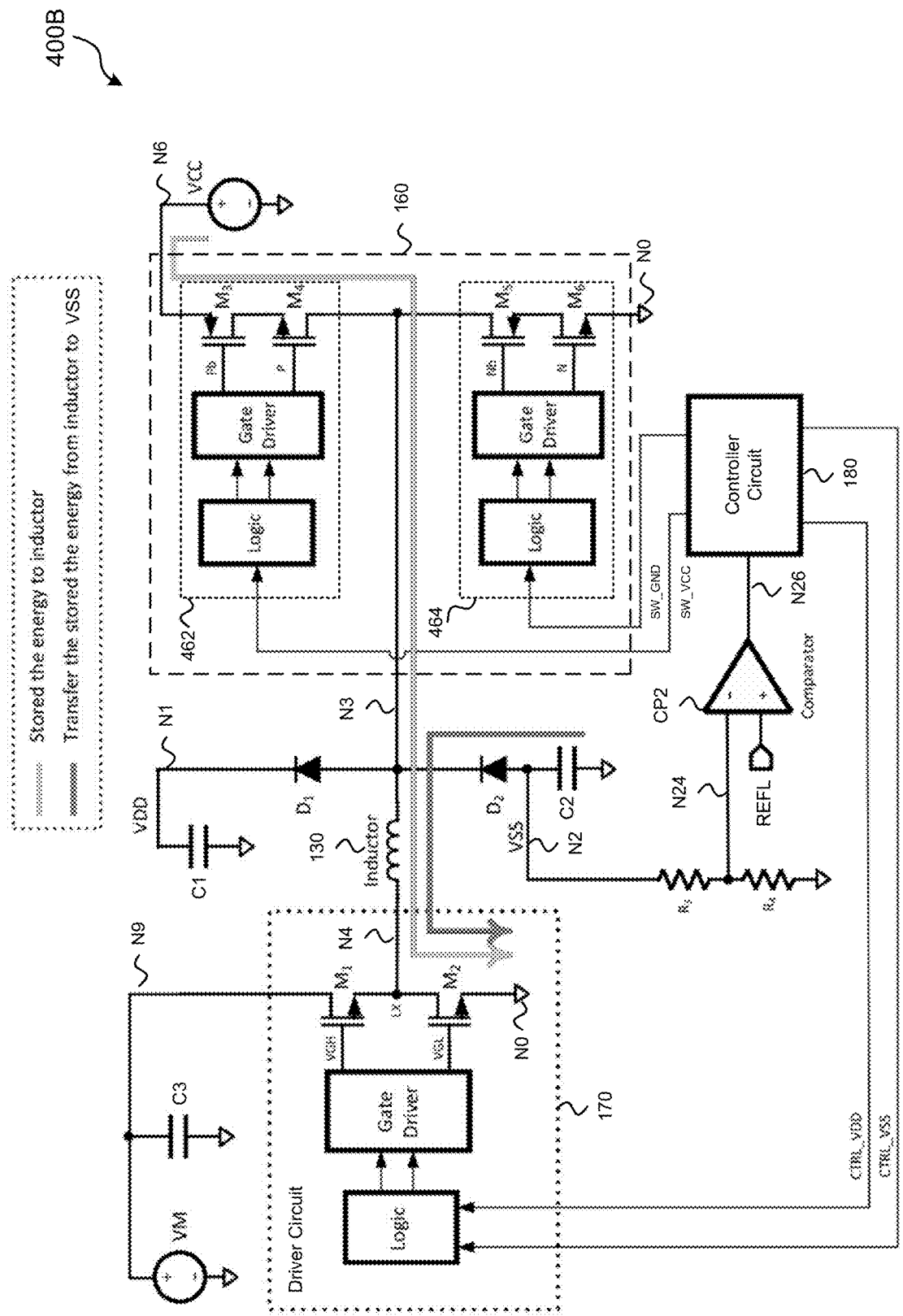
FIG. 4B shows an illustrative schematic that illustrates a second part of the operation of the third example time-multiplexing resonant drive scheme to generate dual polarity supplies in an LC resonance circuit.

FIG. 4A shows an illustrative schematic 400A that illustrates a first part of the operation of a third example time-multiplexing resonant drive scheme to generate dual polarity supplies in an LC resonance circuit. FIG. 4B shows an illustrative schematic 400B that illustrates a second part of the operation of the third example time-multiplexing resonant drive scheme to generate dual polarity supplies in an LC resonance circuit. The examples of FIG. 4A and FIG. 4B are substantially similar to that illustrated in FIGS. 1 and 2, where like components and nodes are similarly labeled. A detailed example implementation of a multiplexer circuit 160 and a driver circuit 170 are also illustrated.

The multiplexer circuit 160 in FIGS. 4A and 4B includes two switch circuits as illustrated by 462 and 464. Each of the switch circuits includes a logic block, a gate driver block and a p-type FET (M3 or M5) and an n-type FETs (M4, M6). The logic block of switch circuits 462 and 464 each receive a portion of the first control signal (e.g., SW_CTL1), which consists of two signals SW_GND and SW_VCC. For example, the logic block of switch circuit 462 receives the signals SW_VCC, while the logic block of switch circuit 464 receives the signal SW_GND. The outputs of each logic block is provided to a respective one of the gate driver blocks. The first gate driver block, for switch circuit 462, provides the signal Pb to a gate of FET M3 and signal P to the gate of FET M4. The second gate driver block, for switch circuit 464, provides the signal Nb to a gate of FET M5 and signal N to the gate of FET M6. When signal SW_VCC is active, the logic and gate driver blocks of switch circuit 462 will activate FETs M3 and M4 vis signals Pb and P to provide a conduction path from the inductor 130 at node N3 to the DC Source at node N6, which corresponds to VCC. When signal SW_GND is active, the logic and gate driver blocks of switch circuit 464 will activate FETs M5 and M6 vis signals Nb and N to provide a conduction path from the inductor 130 at node N3 to the circuit ground at node N0. The logic and gate driver blocks may be combined in function in some example implementations.

The driver circuit 170 in FIGS. 4A and 4B is arranged as a half-bridge driver that includes a logic block a gate driver block, and n-type FETs M1 and M2, similarly arranged as in FIG. 2. The logic block receives the second control signal (e.g., SW_CTL2), which comprises two signals CTRL VDD and CTRL VSS, and generates high and low side switch control signals (e.g., LH and LL). The outputs of the logic block are provided to the gate driver block. The gate driver block, for driver circuit 170, provides the signal VGH to a gate of FET M1 and signal VGL to the gate of FET M2, responsive the switch control signals (e.g., LH and LL). The switched operation of FET M1 and FET M2 should be with sufficient speed so that the first FET M1 and the second FET M2 are not active at the same time, preventing significant switching or shoot-through currents. The logic circuit and the gate driver circuit of driver circuit 170 may be combined in function in some example implementations.

The driver circuits illustrated in FIGS. 2, 4A and 4B are illustrated as including N-type FETS for the first FET and the second FET. However, the specific implementations are not so limited, and other implementations may include P-type FETS, or combinations of N-type and P-type FETS, without departing from the spirit of the present disclosure. Additionally, the logic block and gate drive blocks may be arranged to provide non-overlapping switched operation of N-type FETS, P-type FETS, or any combinations thereof.

The dual polarity supplies (VDD, VSS) can be generated by operation of the driver circuit 170 as a half-bridge resonator, with two switches (back-to-back) that are connected to DC voltage source and ground via operation of the multiplexer. Initially, there may be no stored charge on capacitors C1 or C2, and thus the supply voltages VDD and VSS at nodes N1 and N2 are not at suitable levels (e.g., 0V initially) as may be required. The comparator CP1 (see FIG. 4A) compares the voltage at node N1, via an output of a first voltage divider (R1, R2) at node N21, to a positive reference voltage REFH, and generates a comparator output at node N23. The comparator CP2 (see FIG. 4B) compares the voltage at node N2, via an output of a second voltage divider (R3, R4) at node N24, to a negative reference voltage REFL, and generates a comparator output at node N26. The controller circuit 180 evaluates the voltage at nodes N23 and N26 to determine if the voltages are not at the desired values, and generates one or more control signals (SW_CTL1, SW_CTL2) to start the charging process for the supplies.

As shown in FIG. 4A, when the supply VDD at node N1 is too low, the high-side FET M1of the half-bridge resonator is activated (e.g., VGH is high) while the low-side FET M2 is deactivated (e.g., VGL is low) so that the positive supply may be generated. The switch circuit 464 (see also SW_GND of FIG. 1) will then be modulated with the control signal (SW_GND or SW_CTL1 of FIG. 1) to couple node N3 of the inductor circuit 130 to the circuit ground at node N0. While switch circuit 464 is in a closed circuit operation (e.g., SW_GND is logic high such as 5V), current flows from the battery VM through the driver circuit into the inductor circuit 130 at node N4, where node N3 is coupled to the circuit ground at node N0 through switch circuit 464 and the inductor circuit 130 effectively stores current in a forward direction. While switch circuit 464 is in an open circuit operation (e.g., SW_GND is a logic low such as 0V), the stored energy in the inductor circuit 130 current flows through the diode circuit D1 to node N1, where capacitor C1 stores charge and increases the supply voltage VDD accordingly. Over multiple cycles of this described modulation, the positive supply VDD will increase in value until the desired positive voltage level is achieved, and comparator CP1 will trip to notify the controller circuit 180 that the desired level has been reached. Once the positive supply VDD is at the desired value, the high side switch FET M1 of the driver circuit 170 is deactivated by the controller circuit 180.

As shown in FIG. 4B, when the supply VSS at node N2 is too high, the low-side FET M2 of the half-bridge resonator is activated (e.g., VGL is high) while the high-side FET M1 is deactivated (e.g., VGH is low) so that the negative supply may be generated. The switch circuit 462 (see also SW_VCC of FIG. 1) will then be modulated with the control signal (SW_VCC or SW_CTL1 of FIG. 1) to couple node N3 of the inductor circuit 130 to the DC source at node N6, or VCC. While switch circuit 462 is in a closed circuit operation (e.g., SW_VCC is logic high), current flows from the DC source VCC at node N6 through the inductor circuit 130 at node N3, where node N4 is coupled to the circuit ground at node N0 through the driver circuit 170 and the inductor circuit 130 effectively stores current in a reverse direction. While switch circuit 462 is in an open circuit operation (e.g., SW_VCC is logic low), the stored current in the inductor circuit 130 flows from the ground node N0, through the capacitor C2 and diode circuit D1 to node N3, where energy from the inductor is transferred to capacitor C2 and decreases the supply voltage VSS accordingly. Over multiple cycles of this described modulation, the negative supply VSS will decrease in value (relative to the circuit ground) until the desired negative voltage supply level is achieved, and comparator CP2 will trip to notify the controller circuit 180 that the desired level has been reached. Once the negative supply VSS is at the desired value, the low side switch FET M2 of the driver circuit 170 is deactivated by the controller circuit 180.

The detailed energy storing and transferring paths for the dual supplies are shown by the arrows as indicated on FIGS. 4A and 4B, and also as demonstrated by the waveforms that are similarly labeled in FIG. 3. As illustrated by the above operations, the dual polarity supplies are successfully generated by time multiplexing the operation of the inductor circuit 130. The dual supplies are also generated without the need for an additional boost converter or an additional inverting buck-boost converter, since the multiplexed operation provides all necessary functions without these additional components. Therefore, two bulky inductors can be eliminated from the overall design and a large amount of board area is saved, resulting in a compact form factor that is suitable for wearable devices.

Figure 5:
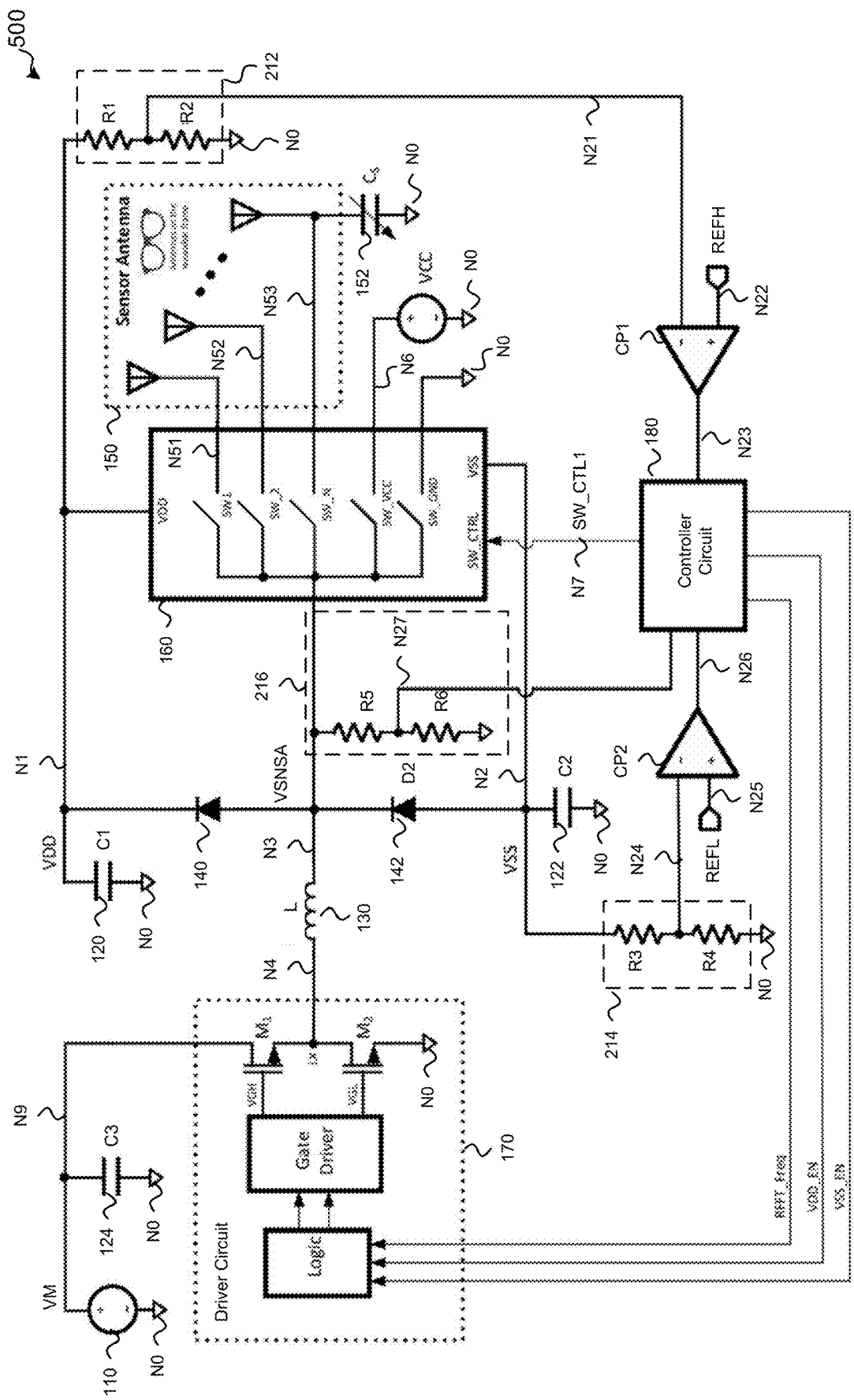
FIG. 5 shows an illustrative schematic of a fourth example time-multiplexing resonant drive scheme to generate dual polarity supplies in an LC resonance circuit that can be used in RF facial detection applications.

FIG. 5 shows an illustrative schematic 500 of a fourth example time-multiplexing resonant drive scheme to generate dual polarity supplies in an LC resonance circuit that can be used in RF facial detection applications. The example of FIG. 5 is substantially similar to that illustrated in FIGS. 1, 3, 4A and 4B, where like components and nodes are similarly labeled. A detailed example implementation of a sensor antenna 150 and a multiplexer 160 are also illustrated in FIG. 5.

The antenna 150 includes multiple individual antennas (e.g., ANT1, ANT2, ..., ANTN), which may be designated as an array (or plurality) of N antennas. Each of the antennas may be physically located at different positions of the wearable frame 190, where each of the N antennas has its own characteristic sense capacitor 152. Each of the antennas has a corresponding port or terminal where the characteristic capacitance is found (e.g., the first antenna at node N51; second antenna at node N52; Nth antenna at node N53). For simplicity, a single sense capacitor is shown, but each antenna has its own sense capacitance value.

MUX 160 includes an input port (e.g., IN) at node N3, a first output port (e.g., OUT1) at node N51, a second output port (e.g., OUT2) at node N52, a third output port (e.g., OUT3) at node N53, a fourth output port (e.g., OUT4) at node N6, a fifth output port (e.g., OUT5) at node N0, a first power port (e.g., VDD) at node N1, a second power port (e.g., VSS) at node N2, and a control port (e.g., CTL) at node N7. Similar to the example of FIGS. 1, 2, 4A and 4B, node N1 corresponds to the positive power supply voltage VDD, node N2 corresponds to the negative power supply voltage VSS, and node N7 corresponds to a first switch control signal SW_CTL1. The control port (SW_CTL) of MUX 160 will selectively couple the input port (IN, node N3) to one of the output ports (OUT1, N51; OUT2, N52; OUT3, N53; OUT4, N6; OUT5, N0), responsive to the input received from the control port (SW_CTL) at node N7, which corresponds to the first switch control signal SW_CTL1.

MUX 160 illustrates five switch circuits. A first switch circuit includes an input at node N3, an output at node N51, and is responsive to a first control signal SW1. A second switch circuit includes an input at node N3, an output at node N52, and is responsive to a second control signal SW2. A third switch circuit includes an input at node N3, an output at node N53, and is responsive to a third control signal SWN. A fourth switch circuit includes an input at node N3, an output at node N6, and is responsive to a fourth control signal SW_VCC. A fifth switch circuit includes an input at node N3, an output at node N0, and is responsive to a fifth control signal SW_GND.

The first switch control signal SW_CTL1 in FIG. 5 can either include multiple individual switch control signals, or be decoded by logic into the individual switch control signals SW1, SW2, SWN, SW_VCC, and SW_GND. Although five output ports and five switch circuits are illustrated in FIG. 5, the number of switch circuits and output ports will vary depending on the number of antennas required in the system implementation. The switch circuits in MUX 160 may be implemented similar to the circuits shown in FIGS. 4A and 4B, for example.

Figure 6A:
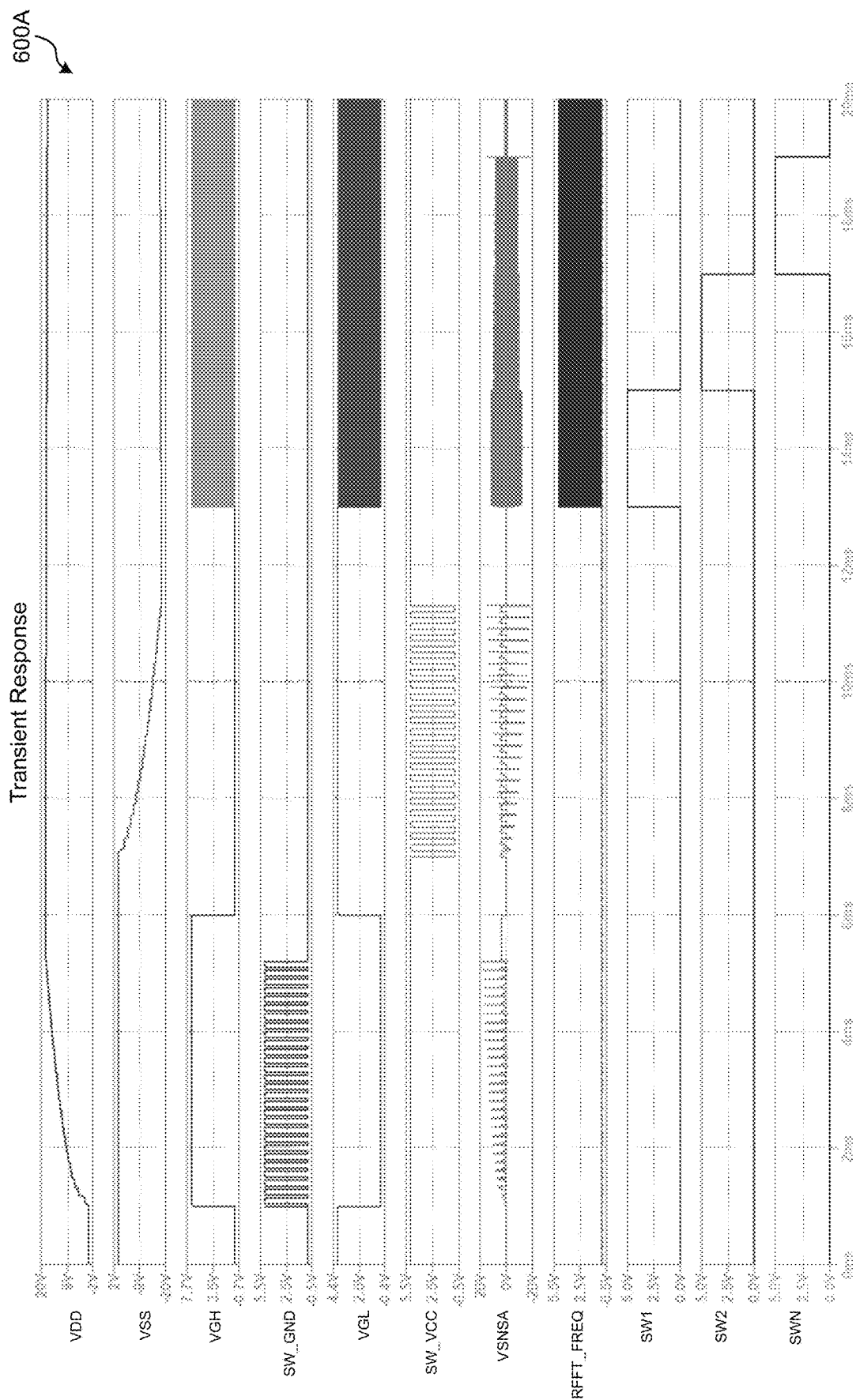
FIG. 6A shows a set of graphs illustrating a transient response for another example time-multiplexing resonant drive scheme that can be used in RF facial detection applications.
Figure 6B:
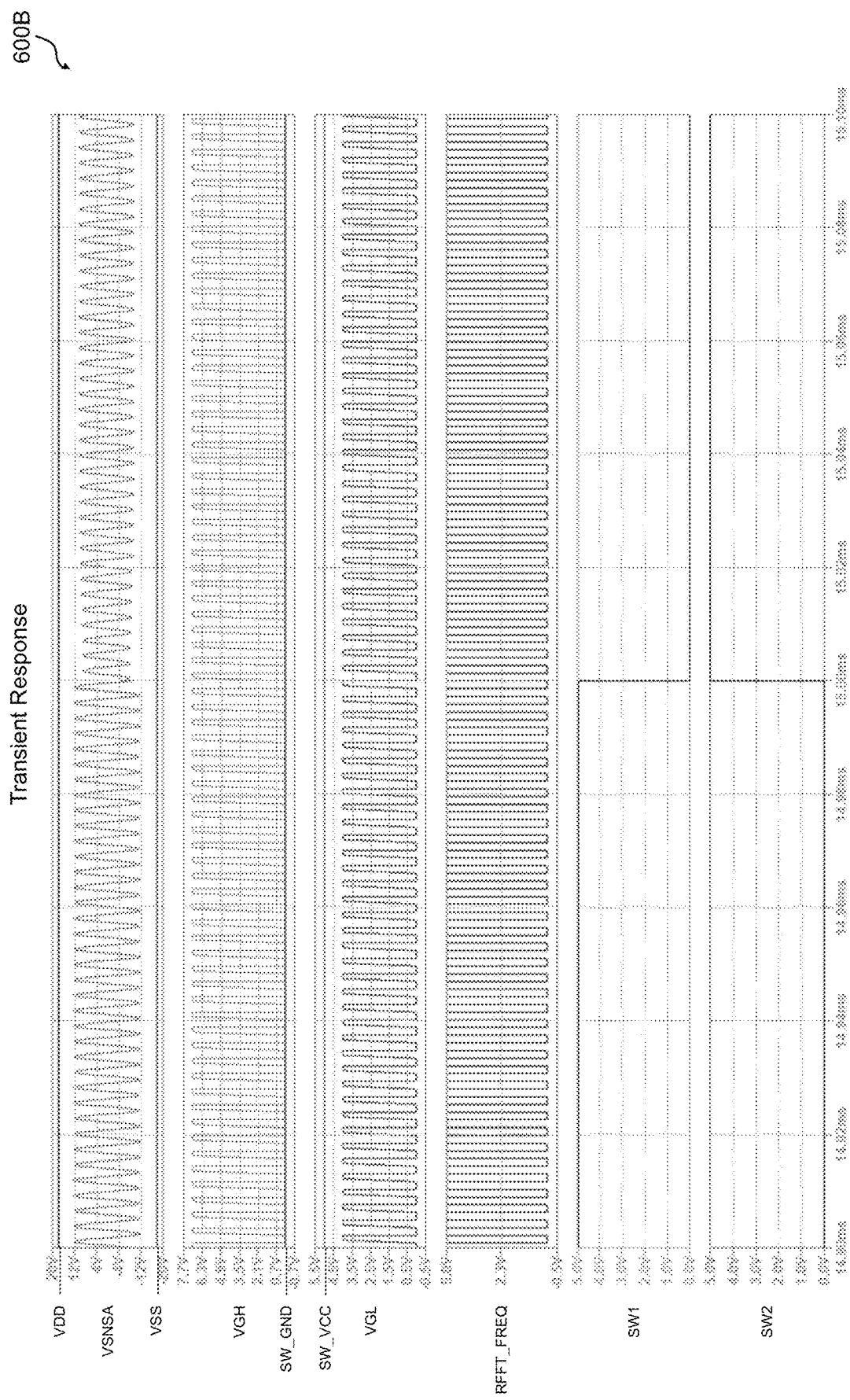
FIG. 6B shows a close in view for the set of graphs of FIG. 6A.

The various operating modes for circuit 500 of FIG. 5 will operate similar to the operating modes of example circuit 100 of FIG. 1, with the addition of further antenna selections as will be illustrated by the discussion of FIGS. 6A and 6B. FIG. 6A shows a first set of graphs illustrating a transient response for another example time-multiplexing resonant drive scheme that can be used in RF facial detection applications such as for FIG. 5. FIG. 6B shows a close in view for the set of graphs of FIG. 6A.

Initially, there may be no stored charge on capacitors C1 or C1, and thus the supply voltages VDD and VSS at nodes N1 and N2 are not at suitable levels (e.g., 0V initially) as may be required. The comparator CP1 is configured to compare the voltage at node N1, via an output of a first voltage divider (212, R1 & R2) at node N21, to a positive reference voltage REFH, and generates a comparator output at node N23. The comparator CP2 is configured to compare the voltage at node N2, via an output of a second voltage divider (214, R3 & R4) at node N24, to a negative reference voltage REFL, and generates a comparator output at node N26. The controller circuit 180 evaluates the voltage at nodes N23 and N26 to determine if the voltages are not at the desired values, and generates one or more control signals (SW_CTL1, SW_CTL2) to start the charging process for the supplies.

Waveforms for the signals VDD, VGH, VGL, and SW_GND are shown in FIG. 6A to illustrate a charging cycle for the positive voltage supply level at node N1. When the supply voltage at node N1 is too low, the high-side FET M1 of the half-bridge resonator (or driver circuit) 170 is activated (e.g., VGH is high) while the low-side FET M2 is deactivated (e.g., VGL is low) so that the positive supply may be generated. One of the switch circuits in MUX 160 will then be modulated to either couple node N3 of the inductor circuit 130 to the circuit ground at node N0 or to decouple node N3 into a high impedance or open circuit condition, as shown by SW_GND in FIG. 6A. Similar to FIG. 4A, current flows from the battery VM through the driver circuit 170 into the inductor circuit 130 at node N4 and the inductor circuit 130 effectively stores energy in a forward direction when SW_GND is logic high (e.g., 5V); and the stored energy in the inductor circuit 130 flows through the diode circuit D1 to node N1, to deliver charge to capacitor C1 when SW_GND is logic low (e.g., 0V). Multiple cycles of this described modulation via SW_GND increases the positive supply voltage, VDD, at node N1 until the desired positive voltage supply level is achieved. Comparator CP1 will trip to notify the controller circuit 180 that the desired level has been reached and the controller circuit 180 will responsively change the switch control signal SW_CTL2 to deactivate the high side switch FET M1 as shown by VGH going low.

Waveforms for the signals VSS, VGH, VGL, and SW_VCC are shown in FIG. 6A to illustrate a charging cycle for the negative voltage supply level at node N2. When the supply VSS at node N2 is too high, the low-side FET M2 of the half-bridge resonator is activated (e.g., VGL is high) while the high-side FET M1 is deactivated (e.g., VGH is low) so that the negative supply may be generated. Another of the switch circuits in MUX 160 will then be modulated to either couple node N3 of the inductor circuit 130 to the DC source VCC at node N6 or to decouple node N3 into a high impedance or open circuit condition, as shown by SW_VCC in FIG. 6A. Similar to FIG. 4B, current flows from the DC source VCC into the inductor circuit 130 at node N3 and the inductor circuit 130 effectively stores energy in a reverse direction when SW_VCC is logic high (e.g., 5V); and the stored energy in the inductor circuit 130 flows through the diode circuit D2 to node N2, to deliver charge to capacitor C2 when SW_VCC is logic low (e.g., 0V). Multiple cycles of this described modulation via SW_GND decreases the negative supply voltage, VSS, at node N2 until the desired negative voltage supply level is achieved. Comparator CP2 will trip to notify the controller circuit 180 that the desired level has been reached and the controller circuit 180 will responsively change the switch control signal SW_CTL2 to deactivate the low side switch FET M2 as shown by VGL going low.

Waveforms for the signals VGH, VGL, RFFT_FREQ, VSNSA, SW1, SW2, and SW2 are shown in FIG. 6A to illustrate a resonance operation of circuit 500 in FIG. 5. A close up view of these waveforms is also shown in FIG. 6B to give a clear view of the operation. The supply levels for VDD and VSS are stable for operation of the LC resonance, as shown by the levels indicated in FIG. 6B. As shown, the controller circuit 180 selects a switch configuration for MUX 160 via the first control signal SW_CTL1 (via SW1), which activates the resonance drive by coupling node N3 to node N51. In this third mode, the controller circuit 180 also selectively activates the driver circuit 170 via the second control signal SW_CTL2 (via RFFT_FREQ), which pulse modulates the coupling of node N4 between node N9 and node N0. The inductor circuit 130 is thus coupled to the first one of the antennas 150 and its characteristic sense capacitor 152 (CS) to form an LC resonant circuit. The dual supply voltages (VDD, VSS) previously generated are used by the various circuits, while the LC resonant circuit is excited by the modulated coupling of node N4 between node N9 and node N0, such that the LC resonant circuit generates an oscillating signal at node N3, as shown by voltage VSNSA. The controller circuit 180, can be configured to capture the sensed voltage at node N27, which may a scaled version of VSNSA such as via voltage divider 216 (R5 and R6). The captured value may correspond to a digital value that can be provided to other systems for further processing (e.g., processing to determine facial expression, movement, etc.).

After the sensed signal for the one antenna is captured, additional processing may be done in a similar fashion to capture the sensed signals for the other antennas. In one example, the processing cycle for the antenna are done one after another as shown by the waveforms of FIGS. 6A and 6B. In other examples, the processing cycles for the antennas may be done after additional charging cycles of either the positive or negative power supply voltages.

Some examples may employ interleaving of the power supply charging cycles and operation of the LC resonance circuit with a selected antenna. In a simple example, the first operating mode for charging VDD is always followed by the second operating mode for charging VSS, followed by the third operating mode of LC resonance operation of each of the antennas in succession. In other examples, the first and second operating modes for charging the dual supply voltages VDD and VSS will only be activated when the supply levels are detected as below a threshold, and the LC resonance operation of each antenna will repeat until such a condition is detected by the controller circuit 180.

In still other examples, the first and second operating modes for charging the dual supply voltages VDD and VSS will be activated once every X cycles of the LC resonance operation. For example, given N antennas their will be N cycles of LC resonance operation required to "scan" all of the antennas, where the value of X may be an integer that is equal to 1, less than N, equal to N, or greater than N. Thus, many implementations are possible depending on the overall system design, the supply levels for VDD and VSS, the size of the capacitors C1 and C2, the number of LC resonance operations required to operate all selected antennas, etc.

The most highlighted aspect of the proposed scheme is a reduced component requirement by time multiplexing the inductor circuits use for multiple purposes. Manufacturing and assembly costs can be reduced, and beneficially achieve reduced overall footprint on circuit area, providing a compact design that is suitable for portable devices.

The disclosure presented herein also encompasses the subject matter set forth in the following clauses:

Example Clause 1: A battery operated device to generate dual supply voltages and sense facial movements of a user by time-multiplexed operation, the device comprising: a first capacitor circuit (120) coupled between a first node (N1) and a circuit ground (N0), wherein the first node (N1) corresponds to a first of the dual supply voltages (VDD); a second capacitor circuit (122) coupled between a second node (N2) and the circuit ground (N0), wherein the second node (N2) corresponds to a second of the dual supply voltages (VSS); an inductor circuit (130) coupled between a third node (N3) and a fourth node (N4); a first diode circuit (140) coupled between the third node (N3) and the first node (N1); a second diode circuit (142) coupled between the second node (N2) and the third node (N3); an antenna (150) coupled to a fifth node (N5), wherein the antenna (150) has a characteristic capacitance that corresponds to a sense capacitor (152) with a capacitance value that varies responsive to the facial movements of the user; a multiplexer (160) that includes an input coupled to the third node (N3), a first output coupled to the circuit ground (N0), a second output coupled to a DC source at a sixth node (N6), and a third output coupled to an antenna (150) at the fifth node (N5), wherein the multiplexer (160) is configured to couple the input to one of the first output, the second output and the third output responsive to a first control signal (SW_CTL1); and a driver circuit (170) that includes a first power terminal coupled to the battery, a second power terminal coupled to the circuit ground, an output coupled to the fourth node (N4), wherein the driver circuit (170) and the multiplexer circuit (160) are configured vias the first and second control signals (SW_CTL1, SWCTL2) to selectively: charge the inductor circuit (130) to generate the dual supply voltages, and drive the inductor circuit (130) with the antenna (150) as a resonance circuit to generate a resonance that varies responsive to facial movement of the user.

Example Clause 2: The device of clause 1, further comprising a controller circuit that is configured to monitor the dual supply voltages and the output of the resonance circuit and adjust the operation of the driver circuit and the multiplexer by adapting the first and second control signals.

Example Clause 3: The device of clause 2, further comprising a voltage divider circuit that is coupled to one of the first node, the second node, and the third node, wherein an output of the voltage divider circuit is coupled to an input of the controller circuit.

Example Clause 4: The device of clause 2, further comprising a voltage divider circuit that is coupled to either the first node or the second node, wherein an output of the voltage divider circuit is coupled to a first input of a comparator circuit, a reference voltage is coupled to a second input of the comparator circuit, and wherein the comparator generates a signal that is coupled to the controller circuit to indicate that the corresponding one of the dual supply voltages has reached a predetermined value that is associated with the reference voltage.

Example Clause 5: The device of clause 2, wherein the controller circuit is configured to adjust the first and second control signals such that energy is coupled from the battery to the inductor circuit, current is stored in the inductor circuit in a forward direction, and the stored current from the inductor circuit is delivered through the first diode circuit to the first capacitor circuit to generate the first power supply voltage in a first mode.

Example Clause 6: The device of clause 5, wherein the driver circuit is configured to couple power from the battery to the fourth node in the first mode, and wherein the multiplexer circuit is configured to pulse modulate a switch circuit between a closed circuit position and an open circuit position, wherein the third node is coupled to the circuit ground in the closed circuit position, and wherein the third node is decoupled from the circuit ground into a high impedance condition in the open circuit position.

Example Clause 7: The device of clause 2, wherein the controller circuit is configured to adjust the first and second control signals such that energy is coupled from the DC source to the inductor circuit, current is stored in the inductor circuit in a reverse direction, and the stored current from the inductor circuit is delivered through the second diode circuit to the second capacitor circuit to generate the second power supply voltage in a first mode.

Example Clause 8: The device of clause 7, wherein the driver circuit is configured to couple the fourth node to the circuit ground in the second mode, and wherein the multiplexer circuit is configured to pulse modulate a switch circuit between a closed circuit position and an open circuit position, wherein the third node is coupled to the DC source in the closed circuit position, and wherein the third node decoupled from the DC source into a high impedance condition in the open circuit position.

Example Clause 9: The device of clause 2, wherein the controller circuit is configured to adjust the first and second control signals such that pulse modulated energy is delivered from the driver circuit to the inductor and antenna of the resonance circuit to excite the resonance circuit and generate an oscillating signal that is observed for face tracking.

Example Clause 10: The device of clause 9, wherein the multiplexer circuit is configured to couple the third node to the fifth node in the third mode, and wherein the driver circuit is configured to pulse modulate the coupling of the fourth node between the battery volage and the circuit ground in the third mode.

Example Clause 11: The device of clause 2, wherein the controller circuit is configured to adjust the operation of the driver circuit and the multiplexer circuit via the first and second control signals such that: the driver circuit couples the fourth node to the battery voltage while the multiplexer circuit modulates the coupling of the third node between the circuit ground and a high impedance condition in a first mode; the driver circuit couples the fourth node to the circuit ground while the multiplexer circuit modulates the coupling of the third node between the DC source and a high impedance condition in a second mode; and the driver circuit modulates the coupling of the fourth node between the battery voltage and the circuit ground while the multiplexer circuit couples the third node to the fifth node in a third mode.

Example Clause 12: The device of clause 11, wherein the controller circuit is configured to adapt the first and second control signals such that the first and second modes are not activated until the supply levels are detected as below a threshold, and the resonance operation of the antenna in the third mode will repeat until the supply levels are detected below the threshold by the controller circuit.

Example Clause 13: The device of clause 1, further comprising a wearable frame, wherein the antenna is positioned about a location on the wearable from, and wherein the characteristic capacitance of the antenna varies based on a distance between the antenna and the skin of the user.

Example Clause 14. The device of clause 13, further comprising a second antenna that is positioned at a different location of the wearable frame, and wherein a second characteristic capacitance of the second antenna varies based on a second distance between the second antenna and the skin of the user.

Example Clause 15: A battery operated device to generate dual supply voltages and sense facial movements of a user by time-multiplexed operation, the device comprising: a first capacitor circuit (120) coupled between a first node (N1) and a circuit ground (N0), wherein the first node (N1) corresponds to a first of the dual supply voltages (VDD); a second capacitor circuit (122) coupled between a second node (N2) and the circuit ground (N0), wherein the second node (N2) corresponds to a second of the dual supply voltages (VSS); an inductor circuit (130) coupled between a third node (N3) and a fourth node (N4); a first diode circuit (140) coupled between the third node (N3) and the first node (N1); a second diode circuit (142) coupled between the second node (N2) and the third node (N3); a first antenna and a second antenna, each coupled to a respective one of a first antenna node (N51) and a second antenna node (N52), wherein each antenna has a characteristic capacitance that corresponds to a sense capacitor (152) with a capacitance value that varies responsive to the facial movements of the user; a multiplexer (160) that includes an input coupled to the third node (N3), a first output coupled to the circuit ground (N0), a second output coupled to a DC source at a sixth node (N6), a third output coupled to the first antenna at the first antenna node (N51), and a fourth output coupled to the second antenna at the second antenna node (N52), wherein the multiplexer (160) is configured to couple the input to one of the first output, the second output, the third output, and the fourth output responsive to a first control signal (SW_CTL1); and a driver circuit (170) that includes a first power terminal coupled to the battery, a second power terminal coupled to the circuit ground, an output coupled to the fourth node (N4), wherein the driver circuit (170) and the multiplexer circuit (160) are configured vias the first and second control signals (SW_CTL1, SWCTL2) to selectively: charge the inductor circuit (130) to generate the dual supply voltages, and drive the inductor circuit (130) with each of the first antenna and the second antenna (150) as a resonance circuit to generate a resonance that varies responsive to facial movement of the user.

Example Clause 16: The device of clause 15 further comprising a wearable frame, wherein the first antenna is positioned about a first location on the wearable from, the second antenna is positioned about a second location on the wearable frame, and wherein the characteristic capacitance of the first and second antennas vary based on a distance between each of the first and second antennas and the skin of the user.

Example Clause 17: The device of clause 15, further comprising a controller circuit that is configured to adjust the operation of the driver circuit and the multiplexer circuit via the first and second control signals such that: the driver circuit couples the fourth node to the battery voltage while the multiplexer circuit modulates the coupling of the third node between the circuit ground and a high impedance condition in a first mode; the driver circuit couples the fourth node to the circuit ground while the multiplexer circuit modulates the coupling of the third node between the DC source and a high impedance condition in a second mode; and the driver circuit modulates the coupling of the fourth node between the battery voltage and the circuit ground while the multiplexer circuit couples the third node to one of the first antenna node and the second antenna node in a third mode.

Example Clause 18: The device of clause 17, wherein the controller circuit is configured to adapt the first and second control signals such that the power supply charging cycles are interleaved with operation of the resonance circuit with the first and second antennas.

Example Clause 19: The device of clause 17, wherein the controller circuit is configured to adapt the first and second control signals such that the first and second modes are not activated until the supply levels are detected as below a threshold, and the resonance operation of each antenna in the third mode will repeat until the supply levels are detected below the threshold by the controller circuit.

Example Clause 20: The device of clause 17, wherein the first and second antennas correspond to two of N antennas in the system, and wherein the controller circuit is configured to adapt the first and second control signals such that the first and second modes are activated once every X cycles of the third mode, wherein X corresponds to an integer that is equal to 1, less than N, equal to N, or greater than N.

It will be understood that the configurations and/or approaches described herein are exemplary in nature, and that these specific embodiments or examples are not to be considered in a limiting sense, because numerous variations are possible. The specific circuits, devices and systems described herein may represent one or more of any number of strategies. As such, various system and/or circuit components may be broken into additional functions or circuits, and/or combined with other functions or circuits as may be desirable in a specific implementation The subject matter of the present disclosure includes all novel and non-obvious combinations and sub-combinations of the various processes, circuits, devices, systems and configurations, and other features, functions and/or properties disclosed herein, as well as any and all equivalents thereof.

We claim:

1. A battery operated device to generate dual supply voltages and sense facial movements of a user by time-multiplexed operation, the device comprising:
    a first capacitor circuit (120) coupled between a first node (N1) and a circuit ground (N0), wherein the first node (N1) corresponds to a first of the dual supply voltages (VDD);
    a second capacitor circuit (122) coupled between a second node (N2) and the circuit ground (N0), wherein the second node (N2) corresponds to a second of the dual supply voltages (VSS);
    an inductor circuit (130) coupled between a third node (N3) and a fourth node (N4);
    a first diode circuit (140) coupled between the third node (N3) and the first node (N1);
    a second diode circuit (142) coupled between the second node (N2) and the third node (N3);
    an antenna (150) coupled to a fifth node (N5), wherein the antenna (150) has a characteristic capacitance that corresponds to a sense capacitor (152) with a capacitance value that varies responsive to the facial movements of the user;
    a multiplexer (160) that includes an input coupled to the third node (N3), a first output coupled to the circuit ground (N0), a second output coupled to a DC source at a sixth node (N6), and a third output coupled to an antenna (150) at the fifth node (N5), wherein the multiplexer (160) is configured to couple the input to one of the first output, the second output and the third output responsive to a first control signal (SW_CTL1); and
    a driver circuit (170) that includes a first power terminal coupled to the battery, a second power terminal coupled to the circuit ground, an output coupled to the fourth node (N4), wherein the driver circuit (170) and the multiplexer circuit (160) are configured via the first and second control signals (SW_CTL1, SWCTL2) to selectively: charge the inductor circuit (130) to generate the dual supply voltages, and drive the inductor circuit (130) with the antenna (150) as a resonance circuit to generate a resonance that varies responsive to facial movement of the user.

2. The device of claim 1, a controller circuit that is configured to monitor the dual supply voltages and the output of the resonance circuit and adjust the operation of the driver circuit and the multiplexer by adapting the first and second control signals.

3. The device of claim 2, further comprising a voltage divider circuit that is coupled to one of the first node, the second node, and the third node, wherein an output of the voltage divider circuit is coupled to an input of the controller circuit.

4. The device of claim 2, further comprising a voltage divider circuit that is coupled to either the first node or the second node, wherein an output of the voltage divider circuit is coupled to a first input of a comparator circuit, a reference voltage is coupled to a second input of the comparator circuit, and wherein the comparator generates a signal that is coupled to the controller circuit to indicate that the corresponding one of the dual supply voltages has reached a predetermined value that is associated with the reference voltage.

5. The device of claim 2, wherein the controller circuit is configured to adjust the first and second control signals such that energy is coupled from the battery to the inductor circuit, current is stored in the inductor circuit in a forward direction, and the stored current from the inductor circuit is delivered through the first diode circuit to the first capacitor circuit to generate the first power supply voltage in a first mode.

6. The device of claim 5, wherein the driver circuit is configured to couple power from the battery to the fourth node in the first mode, and wherein the multiplexer circuit is configured to pulse modulate a switch circuit between a closed circuit position and an open circuit position, wherein the third node is coupled to the circuit ground in the closed circuit position, and wherein the third node is decoupled from the circuit ground into a high impedance condition in the open circuit position.

7. The device of claim 2, wherein the controller circuit is configured to adjust the first and second control signals such that energy is coupled from the DC source to the inductor circuit, current is stored in the inductor circuit in a reverse direction, and the stored current from the inductor circuit is delivered through the second diode circuit to the second capacitor circuit to generate the second power supply voltage in a first mode.

8. The device of claim 7, wherein the driver circuit is configured to couple the fourth node to the circuit ground in the second mode, and wherein the multiplexer circuit is configured to pulse modulate a switch circuit between a closed circuit position and an open circuit position, wherein the third node is coupled to the DC source in the closed circuit position, and wherein the third node decoupled from the DC source into a high impedance condition in the open circuit position.

9. The device of claim 2, wherein the controller circuit is configured to adjust the first and second control signals such that pulse modulated energy is delivered from the driver circuit to the inductor and antenna of the resonance circuit to excite the resonance circuit and generate an oscillating signal that is observed for face tracking.

10. The device of claim 9, wherein the multiplexer circuit is configured to couple the third node to the fifth node in the third mode, and wherein the driver circuit is configured to pulse modulate the coupling of the fourth node between the battery volage and the circuit ground in the third mode.

11. The device of claim 2, wherein the controller circuit is configured to adjust the operation of the driver circuit and the multiplexer circuit via the first and second control signals such that:
the driver circuit couples the fourth node to the battery voltage while the multiplexer circuit modulates the coupling of the third node between the circuit ground and a high impedance condition in a first mode;
the driver circuit couples the fourth node to the circuit ground while the multiplexer circuit modulates the coupling of the third node between the DC source and a high impedance condition in a second mode; and
the driver circuit modulates the coupling of the fourth node between the battery voltage and the circuit ground while the multiplexer circuit couples the third node to the fifth node in a third mode.

12. The device of claim 11, wherein the controller circuit is configured to adapt the first and second control signals such that the first and second modes are not activated until the supply levels are detected as below a threshold, and the resonance operation of the antenna in the third mode will repeat until the supply levels are detected below the threshold by the controller circuit.

13. The device of claim 1, further comprising a wearable frame, wherein the antenna is positioned about a location on the wearable from, and wherein the characteristic capacitance of the antenna varies based on a distance between the antenna and the skin of the user.

14. The device of claim 13, further comprising a second antenna that is positioned at a different location of the wearable frame, and wherein a second characteristic capacitance of the second antenna varies based on a second distance between the second antenna and the skin of the user.

15. A battery operated device to generate dual supply voltages and sense facial movements of a user by time-multiplexed operation, the device comprising:
a first capacitor circuit (120) coupled between a first node (N1) and a circuit ground (N0), wherein the first node (N1) corresponds to a first of the dual supply voltages (VDD);
a second capacitor circuit (122) coupled between a second node (N2) and the circuit ground (N0), wherein the second node (N2) corresponds to a second of the dual supply voltages (VSS);
an inductor circuit (130) coupled between a third node (N3) and a fourth node (N4);
a first diode circuit (140) coupled between the third node (N3) and the first node (N1);
a second diode circuit (142) coupled between the second node (N2) and the third node (N3);
a first antenna and a second antenna, each coupled to a respective one of a first antenna node (N51) and a second antenna node (N52), wherein each antenna has a characteristic capacitance that corresponds to a sense capacitor (152) with a capacitance value that varies responsive to the facial movements of the user;
a multiplexer (160) that includes an input coupled to the third node (N3), a first output coupled to the circuit ground (N0), a second output coupled to a DC source at a sixth node (N6), a third output coupled to the first antenna at the first antenna node (N51), and a fourth output coupled to the second antenna at the second antenna node (N52), wherein the multiplexer (160) is configured to couple the input to one of the first output, the second output, the third output, and the fourth output responsive to a first control signal (SW_CTL1); and
a driver circuit (170) that includes a first power terminal coupled to the battery, a second power terminal coupled to the circuit ground, an output coupled to the fourth node (N4), wherein the driver circuit (170) and the multiplexer circuit (160) are configured via the first and second control signals (SW_CTL1, SWCTL2) to selectively: charge the inductor circuit (130) to generate the dual supply voltages, and drive the inductor circuit (130) with each of the first antenna and the second antenna (150) as a resonance circuit to generate a resonance that varies responsive to facial movement of the user.

16. The device of claim 15 further comprising a wearable frame, wherein the first antenna is positioned about a first location on the wearable from, the second antenna is positioned about a second location on the wearable frame, and wherein the characteristic capacitance of the first and second antennas vary based on a distance between each of the first and second antennas and the skin of the user.

17. The device of claim 15, further comprising a controller circuit that is configured to adjust the operation of the driver circuit and the multiplexer circuit via the first and second control signals such that:
the driver circuit couples the fourth node to the battery voltage while the multiplexer circuit modulates the coupling of the third node between the circuit ground and a high impedance condition in a first mode;

the driver circuit couples the fourth node to the circuit ground while the multiplexer circuit modulates the coupling of the third node between the DC source and a high impedance condition in a second mode; and the driver circuit modulates the coupling of the fourth node between the battery voltage and the circuit ground while the multiplexer circuit couples the third node to one of the first antenna node and the second antenna node in a third mode.

18. The device of claim 17, wherein the controller circuit is configured to adapt the first and second control signals such that the power supply charging cycles are interleaved with operation of the resonance circuit with the first and second antennas.

19. The device of claim 17, wherein the controller circuit is configured to adapt the first and second control signals such that the first and second modes are not activated until the supply levels are detected as below a threshold, and the resonance operation of each antenna in the third mode will repeat until the supply levels are detected below the threshold by the controller circuit.

20. The device of claim 17, wherein the first and second antennas correspond to two of N antennas in the system, and wherein the controller circuit is configured to adapt the first and second control signals such that the first and second modes are activated once every X cycles of the third mode, wherein X corresponds to an integer that is equal to 1, less than N, equal to N, or greater than N.

\* \* \* \* \*